(12) United States Patent
Kermany et al.

(10) Patent No.: US 10,957,422 B2
(45) Date of Patent: Mar. 23, 2021

(54) GENETIC AND GENEALOGICAL ANALYSIS FOR IDENTIFICATION OF BIRTH LOCATION AND SURNAME INFORMATION

(71) Applicant: Ancestry.com DNA, LLC, Lehi, UT (US)

(72) Inventors: Amir R. Kermany, San Francisco, CA (US); Julie M. Granka, San Francisco, CA (US); Keith D. Noto, San Francisco, CA (US)

(73) Assignee: Ancestry.com DNA, LLC, Lehi, UT (US)

( * ) Notice: Subject to any disclaimer, the term of this patent is extended or adjusted under 35 U.S.C. 154(b) by 336 days.

(21) Appl. No.: 15/203,776

(22) Filed: Jul. 6, 2016

(65) Prior Publication Data

US 2017/0011042 A1    Jan. 12, 2017

Related U.S. Application Data

(60) Provisional application No. 62/189,422, filed on Jul. 7, 2015.

(51) Int. Cl.
*G16B 50/00* (2019.01)
*G16B 40/00* (2019.01)
(Continued)

(52) U.S. Cl.
CPC .............. *G16B 50/00* (2019.02); *G16B 40/00* (2019.02); *G16B 10/00* (2019.02); *G16B 30/00* (2019.02)

(58) Field of Classification Search
CPC .... G06F 19/28; G06F 17/3087; G06F 16/436; G06F 19/22; G16B 10/00
(Continued)

(56) References Cited

U.S. PATENT DOCUMENTS 6,277,567 B1 *   8/2001   Graziosi .................. C12Q 1/68
                                                                   435/6.11
6,886,015 B2 *   4/2005   Notargiacomo ........ G06F 16/95
(Continued)

OTHER PUBLICATIONS

PCT International Search Report and Written Opinion, PCT Application No. PCT/IB2016/054094, dated Oct. 25, 2016, 8 pages.
(Continued)

*Primary Examiner* — Ashish Thomas
*Assistant Examiner* — Nargis Sultana
(74) *Attorney, Agent, or Firm* — Fenwick & West LLP

(57) ABSTRACT

A system identifies ancestral birth locations or surnames estimated to be associated with an individual's ancestors using an individual's genetic sample. The system identifies users who are genetic matches to the individual and determines whether and how often a birth location or surname appears in the pedigrees of those users. Birth locations or surnames that appear frequently throughout the pedigrees of genetically matching users may represent birth locations or surnames that are affiliated with the individual's ancestors. The system determines whether the frequency of appearance of a birth location or surname is statistically significant to eliminate biases for certain birth locations or surnames that appear more frequently than others. The birth location or surname may be provided to the individual based on an also-determined enrichment score.

18 Claims, 4 Drawing Sheets

(51) Int. Cl.
*G16B 30/00* (2019.01)
*G16B 10/00* (2019.01)

(58) Field of Classification Search
USPC .................................................. 707/727, 724
See application file for complete search history.

(56) References Cited

U.S. PATENT DOCUMENTS

| | | | | |
|---|---|---|---|---|
| 6,950,753 | B1* | 9/2005 | Rzhetsky | G16B 5/00 702/19 |
| 8,185,557 | B2* | 5/2012 | Slinker | G06F 16/9027 707/797 |
| 8,224,821 | B2* | 7/2012 | Graham | G06Q 10/10 707/736 |
| 9,116,882 | B1* | 8/2015 | Macpherson | G16B 40/00 |
| 2003/0032015 | A1* | 2/2003 | Toivonen | G16B 40/00 435/6.11 |
| 2003/0113756 | A1* | 6/2003 | Mertz | G16H 10/40 435/6.18 |
| 2003/0195707 | A1* | 10/2003 | Schork | G16B 20/00 702/20 |
| 2005/0147947 | A1* | 7/2005 | Cookson, Jr. | G06F 16/2246 434/154 |
| 2005/0149522 | A1* | 7/2005 | Cookson, Jr. | G06F 16/211 |
| 2008/0027656 | A1* | 1/2008 | Parida | G16B 10/00 702/20 |
| 2008/0228751 | A1* | 9/2008 | Kenedy | G06Q 40/00 |
| 2008/0255768 | A1* | 10/2008 | Martin | C12Q 1/6888 702/20 |
| 2009/0100030 | A1* | 4/2009 | Isakson | G06F 16/436 |
| 2009/0299645 | A1* | 12/2009 | Colby | G16H 50/30 702/19 |
| 2010/0218228 | A1* | 8/2010 | Walter | H04N 21/47205 725/105 |
| 2011/0093448 | A1* | 4/2011 | Rafi | G16H 50/70 707/708 |
| 2011/0161168 | A1* | 6/2011 | Dubnicki | G06Q 30/0276 705/14.49 |
| 2012/0218289 | A1* | 8/2012 | Rasmussen | G06F 3/0482 345/619 |
| 2013/0149707 | A1* | 6/2013 | Sorenson | G16B 30/00 435/6.12 |
| 2014/0067355 | A1* | 3/2014 | Noto | G16B 20/00 703/11 |
| 2014/0278138 | A1* | 9/2014 | Barber | G09B 19/0046 702/19 |
| 2015/0100243 | A1* | 4/2015 | Myres | G16B 20/00 702/19 |

OTHER PUBLICATIONS

King, T. et al., "What's in a Name? Y Chromosomes, Surnames and the Genetic Genealogy Revolution," Trends in Genetics, 2009, pp. 351-360, vol. 25, No. 8.

Browning, S.R. et al., "Rapid and Accurate Haplotype Phasing and Missing-Data Inference for Whole-Genome Association Studies by Use of Localized Haplotype Clustering," The American Journal of Human Genetics, Nov. 2007, pp. 1084-1096, vol. 81.

Gusev, A. et al., "Whole Population, Genome-Wide Mapping of Hidden Relatedness," Genome Research, 2009, pp. 318-326, vol. 19.

Noto, K. et al., "Underdog: A Fully-Supervised Phasing Algorithm That Learns from Hundreds of Thousands of Samples and Phases in Minutes," Oct. 20, 2014, 1 page.

European Patent Office, Extended European Search Report, European Patent No. 16820936.9, dated Feb. 5, 2019, 13 pages.

Genealogy Blog with Attitude, "'Surnames, 23andMe, and AncestryDNA: Making the Most of Match Counts and "Enrichment"'—Genealogy and Genomics," Apr. 4, 2015, 24 pages, [Online] Retrieved Jan. 23, 2019, Retrieved from the Internet: <URL: http://web.archive.org/web/20150404210843/http://ourpuzzlingpast.com/geneblog/2015/01/25/surnames-23andme-and-ancestrydnamaking-the-most-of-match-counts-and-enrichment>.

Wikipedia, "Identity by descent," Feb. 13, 2015, 5 pages, [Online] Retrieved Jan. 23, 2019, Retrieved from the Internet: <URL:https://en.wikipedia.org/w/index.php?title=identity_by_descent&oldid=646873616.

* cited by examiner

GENETIC AND GENEALOGICAL ANALYSIS FOR IDENTIFICATION OF BIRTH LOCATION AND SURNAME INFORMATION

CROSS REFERENCE TO RELATED APPLICATIONS

This application claims the benefit of U.S. Provisional Application No. 62/189,422, filed Jul. 7, 2015, which is incorporated by reference in its entirety.

BACKGROUND

This description generally relates to population analyses on human genetic and genealogical information, and particularly to using that information to identify ancestral birth locations or ancestral surnames for an individual.

An individual may often be interested in learning more about his/her ancestral history including ancestral birth locations and/or ancestral surnames. Families may have genealogical pedigrees or family trees that may be verbally passed down from generation to generation. However, these genealogical family trees become inaccurate as they are passed along or may be missing the birth location or surnames of past ancestors altogether. Therefore, an individual often cannot rely on genealogical data provided by a family member to identify ancestral birth locations or surnames.

SUMMARY

Described embodiments identify likely birth locations and surnames of an individual's ancestors based on the individual's genotype, genotypes of a population of users who are genetic matches to the individual, and genealogical data (e.g. pedigree or family tree) of those matches. Note that no genealogical data for the individual is necessary for this identification to be performed.

In one embodiment, to generate identifications of possible ancestral birth locations and/or surnames for an individual, a birth location and surname identification system receives a genetic sample from the individual. The individual's genetic sample is sequenced and is analyzed to identify users in the system who are genetic matches to the individual. At least some of those genetically matched users will have an associated pedigree that identifies birth locations and/or surnames of their ancestors. A computer system determines the frequency of appearance of a birth location or surname amongst the pedigrees of the genetically matched users and further determines whether that frequency of appearance is of statistical significance. In various embodiments, the system performs a statistical test to prevent recommending birth locations or surnames that may be disproportionally represented. If the frequency of appearance of the birth location or surname is deemed statistically significant, the system may present it to the individual as a recommended ancestral birth location or surname.

BRIEF DESCRIPTION OF THE DRAWINGS

These and other features, aspects, and advantages of the present invention will become better understood with regard to the following description, and accompanying drawings, where.

Figure 1:
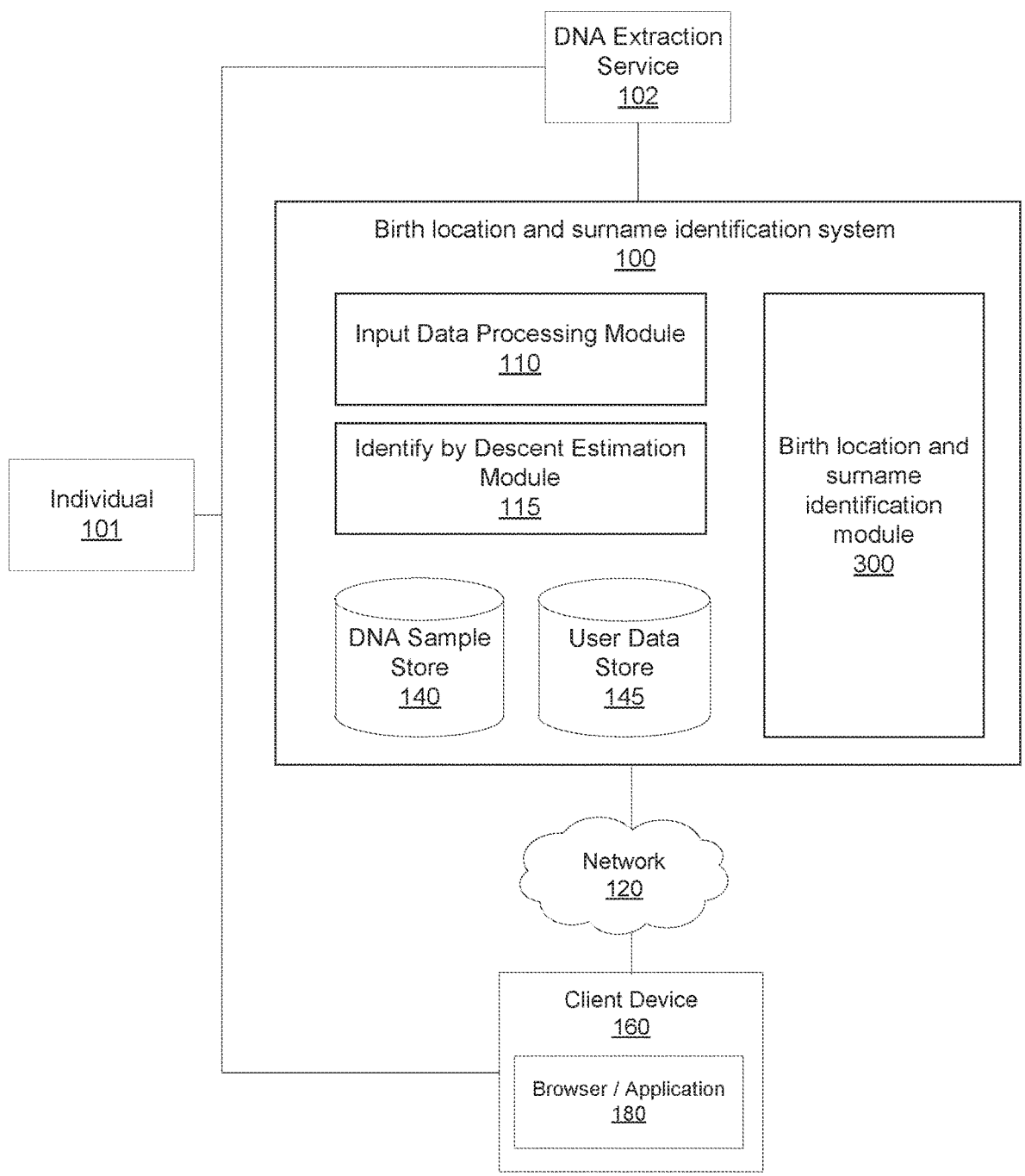
FIG. 1 is a block diagram of an overview of a computing system for identifying an ancestral birth location or surname to an individual, according to one embodiment.

Note that for purposes of clarity, only one of each item corresponding to a reference numeral is included in most figures, but when implemented, multiple instances of any or all of the depicted modules may be employed, as will be appreciated by those of skill in the art.

DETAILED DESCRIPTION

Environment Overview

FIG. 1 is a block diagram of an overview of a computing system for identifying an ancestral birth location or surname to an individual, according to one embodiment. Depicted in FIG. 1 are an individual 101 (i.e. a human or other organism), a DNA extraction service 102, a birth location and surname identification system 100, a network 120, and a client device 160.

Individual 101 provides a DNA sample for analysis. In one embodiment, an individual 101 uses a sample collection kit to provide a DNA sample, e.g., saliva, from which genetic data can be reliably extracted according to conventional DNA processing techniques. DNA extraction service 102 receives the sample and estimates genotypes from the genetic data, for example by extracting the DNA from the sample and identifying genotype values of single nucleotide polymorphisms (SNPs) present within the DNA. The result in this example is a diploid genotype for each SNP. The birth location and surname identification system 100 receives the genetic data from DNA extraction service 102 and stores the genetic data in a DNA sample store 140 containing DNA diploid genotypes. The genetic data stored in the DNA sample store 140 may be associated with the individual 101 in the user data store 145 via one or more pointers.

Identifying ancestral birth locations or surnames that may be associated with a given individual involves analyzing genealogical information of other individuals that are genetic matches with the individual. To determine the genetic matches, analysis of identity-by-descent (IBD) is used. IBD analysis can be used to identify the familial relationship between any two people (e.g., second cousins) in a population as long as the relationship is due to shared common ancestors from the recent past (e.g., on the order of several hundred years). To date, IBD analysis has not been successfully used to accurately identify ancestral birth locations or surnames from an individual's genetic data.

To perform IBD, the birth location and surname identification system 100 includes an input data processing module 110 that processes the DNA to identify shared segments of DNA data between the individual 101 and a number of other users whose DNA is already stored by the system. An IBD estimation module 115 uses the shared segments of DNA are used to identify those other users known in the user data store 145 whose genetic data is stored in the DNA sample store 140 who are matches to the individual. The birth location and surname identification module 300 uses the match information to access genealogical data of the individual's 101 genetic matches in order to identify possible surnames and birth locations for the ancestors of the individual 101.

Each of these modules is described in further detail below. The breakdown of the logical functions of the system 100 into the above-introduced modules is for clarity of description only. In other embodiments, the computer system 100 may comprise more or fewer modules, and the logical structure may be differently organized. The data stores may be represented in different ways in different embodiments, such as comma-separated text files, or as databases such as relational databases (SQL) or non-relational databases (NoSQL).

The network 120 facilitates communications amongst one or more client devices 160 and the system 100. The network 120 may be any wired or wireless local area network (LAN) and/or wide area network (WAN), such as an intranet, an extranet, or the Internet. In various embodiments, the network 120 uses standard communication technologies and/or protocols. Examples of technologies used by the network 120 include Ethernet, 802.11, 3G, 4G, 802.16, or any other suitable communication technology. The network 120 may use wireless, wired, or a combination of wireless and wired communication technologies. Examples of protocols used by the network 120 include transmission control protocol/Internet protocol (TCP/IP), hypertext transport protocol (HTTP), simple mail transfer protocol (SMTP), file transfer protocol (TCP), or any other suitable communication protocol.

A client device 160 is a computing device capable of transmitting and/or receiving data via the network 120. In various embodiments, the client device 160 belongs to the individual 101 that provided the genetic sample. Examples of client devices 160 include desktop computers, laptop computers, tablet computers (pads), mobile phones, personal digital assistants (PDAs), gaming devices, or any other electronic device including computing functionality and data communication capabilities. The client device 160 may use a web browser 180, such as Microsoft Internet Explorer, Mozilla Firefox, Google Chrome, Apple Safari and/or Opera, as an interface to connect with the network 120. Additionally or alternatively, specialized application software 180 that runs native on a mobile device is used as an interface to connect to the network 120.

The birth location and surname identification system 100 sends, through the network 120, a list of surnames or birthplaces to the client device 160 identified by system 100 for presentation to the individual 101. The list of surnames or birthplaces may be presented by the client device 160 on a user interface or a display screen.

Although not necessarily a part of any particular illustrated module, a new user to the system 100 who is submitting their DNA among other data will activate a new account, often through graphical user interface (GUI) provided through a mobile software application or a web-based interface. As part of the account activation process, the system 100 receives one or more types of basic personal information about the individual 101 such as age, date of birth, geographical location of birth (e.g., city, state, county, country, hospital, etc.), complete name including first, last middle names as well as any suffixes, and gender. This received user information is stored in the user data store 145, in association with the corresponding DNA samples stored in the DNA sample store 140.

Genetic Data Processing

To process the data stored in the DNA sample store 140 and estimate IBD from the DNA samples, the computing system 100 comprises an input data processing module 110, and an IBD estimation module 115. These modules are described in relation with FIG. 2 which is a flow diagram for the operation of the computer system 100 for estimating and storing estimated IBD in accordance with an embodiment.

II.a. DNA Sample Receipt and Account Creation

Figure 2:
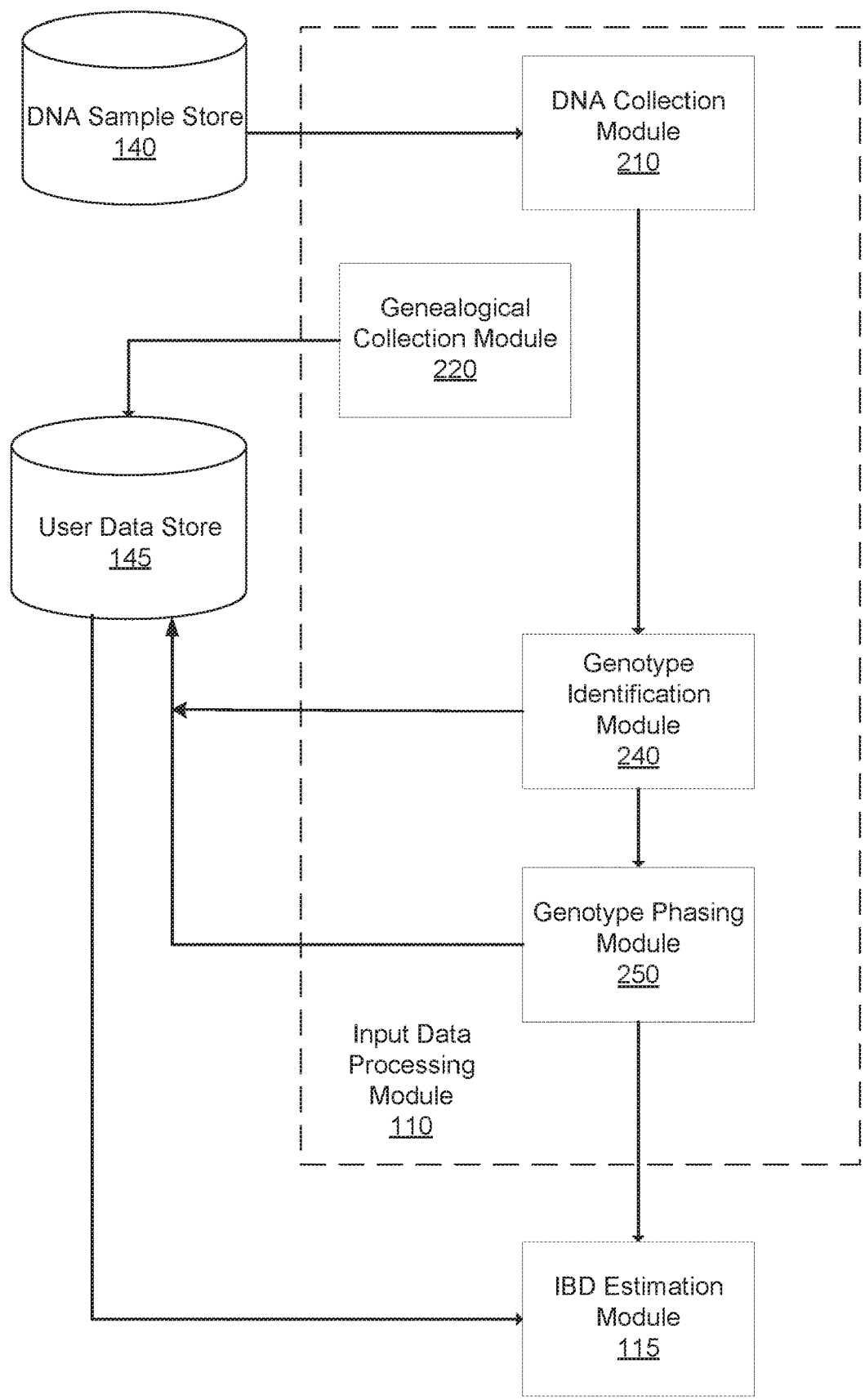
FIG. 2 is a flow diagram for the operation of the computer system for receiving, processing and storing genetic and genealogical data associated with users of the system in accordance with an embodiment.

FIG. 2 is a flow diagram for the operation of the computer system for receiving, processing and storing genetic, genealogical and survey input data. The input data processing module 110 is responsible for receiving, storing and processing data received from an individual 101 via the DNA extraction service 102. The input data processing module 110 includes a DNA collection module 210, a genealogical collection module 220, genotype identification module 240, and a genotype phasing module 250.

The DNA collection module 210 is responsible for receiving sample data from external sources (e.g., extraction service 102), processing and storing the samples in the DNA sample store 140. The data stored in the DNA sample store 140 may store one or more received samples DNA linked to a user as a <key, value> pair associated with the individual 101. In one instance, the <key, value> pair is <sampleID, "GA TC TC AA">. The data stored in the DNA sample store 140 may be identified by one or more keys used to index one or more values associated with an individual 101. In one example, keys are a userID and sampleID, or alternatively another <key, value> pair is <userID, sampleID>. In various embodiments, the DNA sample store 140 stores a pointer to a location associated with the user data store 145 associated with the individual 101. The user data store 145 will be further described below.

II.b. Genealogical Data

The genealogical collection module 220 both receives and processes genealogical data and stores the data in the user data store 145. This data may be received for the individual 101, and may have been received in the past for other users of the system, some of whom may be determined to be genetic matches to the individual 101.

The genealogical data may include a variety of different types of information. The genealogical data can take the form of a pedigree of a user (e.g., the recorded relationships in a family). To collect the data, the genealogical collection module 220 may be configured to provide an interactive GUI that asks the user questions or provides a menu of options, and receives user input that can be processed to obtain the genealogical data. Examples of genealogical data that may be collected include, but are not limited to, names (first, last, middle, suffixes), birth locations (e.g., county, city, state, country, hospital, global map coordinates), date of birth, date of death, marriage information, family relations (manually provided rather than genetically identified), etc. These data may be manually provided or automatically extracted via, for example, optical character recognition (OCR) performed on census records, town or government records, or any other item of printed or online material.

The pedigree information associated with a user may include a genealogical graph. For example, the genealogical graph may include one or more specified nodes. Each specified node in the genealogical graph represents either the user or an ancestor of the user that could have passed down genetic material to the user.

The pedigree information provided by users may or may not be accurate or complete. The genealogical collection module 220 is responsible for filtering the received pedigree data based on one or more quality criteria in an effort to discard lower quality genealogical data. For example, the genealogical collection module 220 may filter the received pedigree data by excluding all pedigree nodes associated with a stored DNA sample that do not satisfy all of the following criteria: (1) recorded death date for a the linked pedigree node corresponds to official records (when available), (2) the gender is the same as the gender provided by the user; and (3) the birth date is within 3 years of the birth date provided by the user. The user may be prompted via GUI to resolve any discrepancies identified by module 220. In some embodiments, all received genealogical data marked as "private" are excluded from the any subsequent analysis to ensure that any privacy requirements imposed on the data are met.

II.c. Processing and Phasing DNA Samples

The genotype identification module 240 accesses the collected DNA data from the DNA collection module 210 or the sample store 140 and identifies autosomal SNPs so that the individual's diploid genotype on autosomal chromosomes can be computationally phased. The genotype identification module 240 provides the identified SNPs to the genotype phasing module 250 which phases the individual's diploid genotype based on the set of identified SNPs. The genotype phasing module 250 generates a pair of estimated haplotypes for each diploid genotype. The estimated haplotypes are then stored in the user data store 145 in association with the individual 101, and may also be stored in association with or verified against the genotypes of the individual's parents, who may also have their own separate accounts in the system 100. A variety of different computational phasing techniques may be used including, for example, the techniques described in U.S. Patent Application No. 2016/061,568, filed on Jan. 17, 2014, which is hereby incorporated by reference in its entirety. The phasing module 250 stores phased genotypes in the user data store 145.

II.d. IBD Estimation

The IBD estimation module 115 is responsible for identifying IBD segments (also referred to as IBD estimates) from phased genotype data (haplotypes) between the individual 101 and a user stored in the user data store 145. IBD segments are chromosome segments identified in the individual 101 and a user that are putatively inherited from a recent common ancestor. Typically, an individual 101 and a user who are closely related share a relatively large number of IBD segments, and the IBD segments tend to have greater length (individually or in aggregate across one or more chromosomes). Alternatively, an individual 101 and a user who are more distantly related share relatively few IBD segments, and these segments tend to be shorter (individually or in aggregate across one or more chromosomes).

In one embodiment, the IBD estimation algorithm used by the IBD estimation module 115 to estimate (or infer) IBD segments between an individual 101 and a user is as described in U.S. patent application Ser. No. 14/029,765, filed on Sep. 17, 2013, which is hereby incorporated by reference in its entirety. Another further processing step may be performed on these inferred IBD segments by applying the technique described in PCT Patent Application No. PCT/US2015/055579, filed on Oct. 14, 2015, which is hereby incorporated by reference in its entirety. The identified IBD segments are stored in the user data store 145 in association with the individual 101.

The IBD estimation module 115 is configured to estimate IBD segments between the individual 101 and large numbers of users stored in the user data store 145. In some embodiments of this module, the computing system has been optimized to efficiently handle large amounts of IBD data. Said another way, IBD is estimated across a large number of individuals based on their DNA. For example, in one implementation, the IBD estimation module 115 (and computing system 100 generally) distributes IBD computations over a Hadoop computing cluster, internal to or external from computing system 100, and stores the phased genotypes used in the IBD computations in a database so that IBD estimates for new accounts/individuals can be quickly compared to previously processed individuals.

Birth Location and Surname Identification System

III.a. Identifying Genetic Matches

Figure 3:
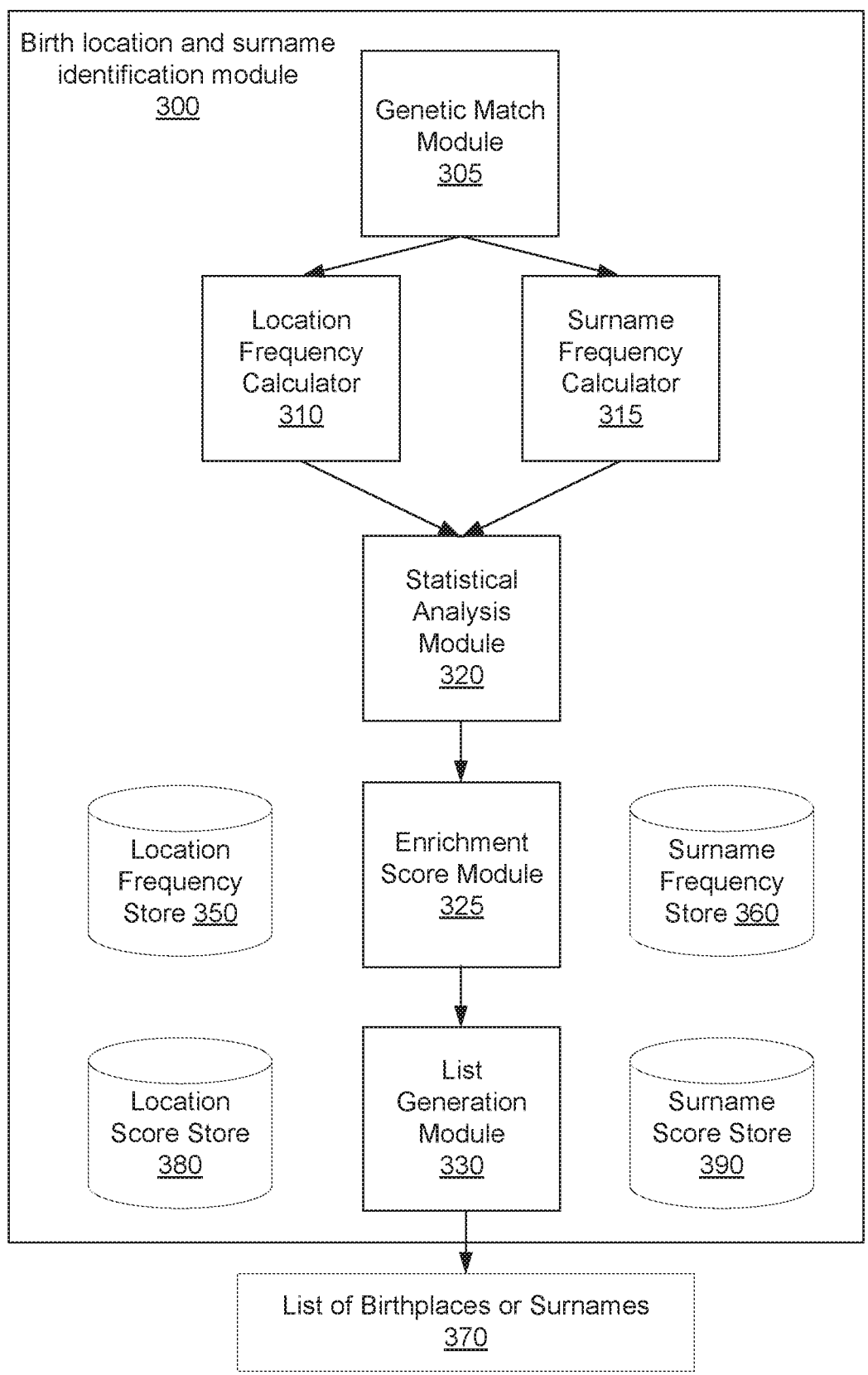
FIG. 3 is a flow diagram for the operation of the birth location and surname identification module, in accordance with an embodiment.

FIG. 3 depicts the birth location and surname identification module 300, in accordance with an embodiment. The birth location and surname identification module 300 includes a genetic match module 305, a location frequency calculator 310, a surname frequency calculator 315, a statistical analysis module 320, an enrichment score module 325, a list generation module 330, a location frequency store 350, a surname frequency store 360, a location score store 380, and a surname score store 390.

The genetic match module 305 retrieves the IBD estimates between the individual 101 and the users in the user data store 145 and determines whether the individual 101 and any given other user are a genetic match. In one embodiment, the individual 101 and a user are a match if they have higher than a threshold amount of IBD segment sharing, as determined by the IBD estimation module 115. A match may indicate that the individual 101 and the user are related (e.g. parent/child, sibling, aunt/uncle, first cousin, first cousin once removed, second cousin, second cousin once removed). The genetic match module 305 identifies all users in the user data store 145 that are considered matches to the individual 101. The set of user matches is referred to herein by $M_u$. In an example, the number of matches is limited to the top 3000 matches (i.e. $|M_u| \leq 3000$) sorted based on amount of IBD segment sharing.

III.b. Match and Background Frequency for a Birth Location

The genetic match module 305 provides the set of user genetic matches, $M_u$, to the location frequency calculator 310 to determine an identification of possible birth locations associated with the user. The location frequency calculator 310 determines how frequently a particular birth location appears amongst the pedigrees of the users within the set of user matches, $M_u$. To do this, the location frequency calculator 310 retrieves, for each matching user in the set of user matches $M_u$, the matching user's pedigree. The pedigree includes a genealogical graph from the user data store 145. For example, a genealogical graph in the pedigree may be the matching user's family tree that describes the relationship between the matching user and each of the matching user's relatives. Each relative in the matching user's pedigree has associated genealogical data such as the relative's birth location.

For a given matching user $v \in M_u$, $T_v$ denotes a set of birth locations indicated in matching user v's pedigree. For each matching user, the location frequency calculator 310 identifies the set of birth locations, $T_v$, in the matching user's pedigree. For example, the location frequency calculator 310 may identify a matching user v as having 10 relatives born in New York City, 2 relatives born in Boston, and 2 relatives born in Los Angeles. Therefore, the elements in $T_v$ include New York City, Boston, and Los Angeles. A presence indicator $a_{v,i}$, may be represented by the indicator function representing whether a birth location i is indicated in matching user v's pedigree:

$$a_{v,i} = \begin{cases} 1 & \text{if } i \in T_v \\ 0 & \text{otherwise} \end{cases}, \quad (1)$$

Thus, for this example, matching user v has an indicator function score of 1 for birth locations of New York City, Boston, and Los Angeles. All other birth locations (e.g. Washington D.C., elsewhere) would have a presence indicator and corresponding indicator function score of 0.

The location frequency calculator 310 repeats this process for the set of matches $M_u$. For a given birth location, i, the total number of pedigrees ($m_i$) of users in the set of matches that have this birth location is determined according to:

$$m_i = \sum_{v \in M_u} a_{v,i} \qquad (2)$$

For example, the location frequency calculator 310 summates the indicator function score for each birth location. Thus, if the number of matching users is 1000, the maximum number of pedigrees ($\max(m_i)$) that have the birth location is 1000, which would occur if every user in the set of matches $M_u$ has the birth location in their pedigree.

The location frequency calculator 310 uses the total number of pedigrees $m_i$, to determine $p_i$, the match frequency of a birth location i, where $p_i$ is determined according to:

$$p_i = m_i / |M_u| \qquad (3)$$

where $|M_u|$ is the total number of matching users in the set $M_u$. Returning to the previous example, if all 1000 users in the set of matches $M_u$ (e.g. $|M_u|=1000$) had the birth location of New York City in their pedigree (e.g. $m_i=1000$), then the match frequency of New York City is $p_{New\ York\ City}=1$. Therefore, the match frequency of a birth location represents how often matching users in the set of matches $M_u$ are associated with the birth location, which can be used as a way of determining an association between the ancestors of the individual 101 and the birth location. This match frequency is stored in the location frequency store 350.

The location frequency calculator 310 also calculates a background frequency for each birth location i. The background frequency of a birth location provides an indication as to how often the birth location appears amongst the greater population of users stored in the system, including those who are not matches to the individual. For example, high population cities such as New York City or Boston may have higher background frequencies than smaller cities such as Cheyenne, Wyo. Here, D represents the total set of users in the system. Generally the number of users in set D is significantly larger (e.g. multiple orders of magnitude larger) than the number of matching users in the set of matches $M_u$. Each user in D may have a corresponding pedigree. Altogether, this forms the set of all pedigrees stored in the user data store 145.

To determine the background frequency, the location frequency calculator 310 may use a similar indicator function as was previously shown in equation (1) to calculate whether a birth location i, exists in the pedigree corresponding to user w in the set D:

$$a_{w,i} = \begin{cases} 1 & \text{if birth location, } i, \text{ exists in user } w's \text{ pedigree} \\ 0 & \text{otherwise} \end{cases} \qquad (4)$$

The location frequency calculator 310 summates the total number of pedigrees that each have the birth location, each pedigree corresponding to a user w in the set of D. To calculate the background frequency, the location frequency calculator 310 divides the summated total number of users in the set of D that have the birth location by the total number of users in the set of D. Therefore, the background frequency of a birth location, i, is expressed in equation 5 as $$q_i = \frac{1}{|D|} \sum_{w \in D} a_{w,i} \qquad (5)$$

This background frequency is stored in the location frequency store 350.

III.c. Match and Background Frequency for a Surname

The surname frequency calculator 315 calculates a match frequency and background frequency for each surname in the pedigrees of matching users in a similar fashion as was discussed for birth locations in section III.b. The surname frequency calculator 315 receives the set of user matches, $M_u$, from the genetic match module 305 for an individual 101 and determines a match frequency $p_j$, that represents how often a given surname, j (e.g. Bradley, O'Malley, Johnson), appears amongst the pedigrees of users, v, in the set of user matches, $M_u$. For example, for a surname "Bradley" (e.g. j="Bradley"), $$p_j = \frac{\sum_{v \in M_u} a_{v,j}}{|M_u|} \qquad (6)$$

where $a_{v,j}$ is the indicator function previously described in equation (1). The surname frequency calculator also calculates the background frequency for the surname "Bradley" in the total set of users in the system, D.

$$q_j = \frac{1}{|D|} \sum_{w \in D} a_{w,j} \qquad (7)$$

The match frequency, $p_j$, and background frequency, $q_j$, may each be stored in the surname frequency store 360.

Often, there will be many more surnames in the user store 145 than birth locations. Many of those surnames will be similar to others, with only minor variations in spelling. Unmodified, these variant spellings may reduce the efficacy of the surname frequency calculation. To address this, the surname frequency calculator 315 may first normalize, meaning that the surname frequency calculator 315 may consider many alternate spellings as being the same surname for purposes of frequency calculations. Examples of such alternate spellings may include use of characters not used in English (e.g., "o" versus "ø"); capitalization, punctuation, and spacing ("O'Malley" versus "Omalley"); suffixes ("Jr."); and commentary ("Johnson (WWII Veteran)"). A simple normalization is performed that ignores capitalization and punctuation, and removes commentary, thereby reducing the set of surnames under consideration. Alternate spellings and misspellings may be interpreted by the surname frequency calculator 315 as a different surname.

III.d Calculating the Statistical Likelihood

The statistical analysis module 320 identifies which birth locations and surnames are sufficiently notable for the individual 101 under consideration so as to merit possibly providing to the individual 101 as likely being associated with their own ancestors.

For example, there may be a total of 1000 users in the set of matches, $M_u$. Assume that 10% of the users that are in the set of matches, $M_u$, have a particular birth location in their pedigree (i.e. $m_i=100$, therefore $p_i=0.1$). A match frequency, $p_i$, of 10% may appear to be a very high number of appearances for a birth location. However, if the background frequency, $q_i$, is also close to 10%, meaning that the birth location appears approximately equally frequently in the pedigrees of all users in the system, then a match frequency, $p_i$, of 10% may not be sufficiently notable to be worth identifying as associated with the individual.

The statistical analysis module 320 receives the match frequency, $p_i$, and background frequency, $q_i$, for all different birth locations, i, from the location frequency calculator 310.

The statistical analysis module 320 conducts a statistical analysis test to determine whether the match frequency of a given birth location is sufficiently notable. For each birth location, i, the statistical analysis module 320 determines the likelihood of observing the received match frequency, $p_i$, and background frequency, $q_i$ under a null hypothesis $H_0$ scenario. An example of a null hypothesis $H_0$ is the assumed scenario where the match frequency and background frequency are the same (i.e. $p_i=q_i$). Conversely, the alternative hypothesis $H_1$ is the assumed scenario where the match frequency and background frequency are non-equal (i.e. $p_i \neq q_i$), with the assumption that if, particularly, $p_i > q_i$, then $p_i$, and thus i, may be statistically significant and therefore worth possibly providing to the individual.

Therefore, the statistical analysis module 320 determines the likelihood of observing the received match frequency and background frequency under the assumption that the match frequency, $p_i$, and background frequency, $q_i$, are equal. However, if the received match frequency is sufficiently larger than the received background frequency, then the null hypothesis $H_0$ is rejected in favor of the alternative hypothesis $H_1$. What constitutes a sufficient difference between the received match frequency, $p_i$, and background frequency, $q_i$, will be discussed further below in regards to the summary statistic $S_i$.

A similar calculation may be performed for surnames by receiving the match frequency, $p_j$, and background frequency, $q_j$, for all surname identifications, j, from the surname frequency calculator 315. The subsequent discussion focuses on conducting a statistical test for a birth location, i. This discussion may also refer to conducting a statistical test for a surname.

The statistical test is performed under a null hypothesis $H_0$, the assumed scenario where the match frequency, $p_i$, and the background frequency, $q_i$, are equal. In various embodiments, the statistical analysis module 320 conducts a maximum likelihood ratio test. In other examples, the statistical analysis test may be a Pearson's chi-squared test, a Z-test, or a F-test. The test statistic, $\Lambda$, for the maximum likelihood ratio test is determined according to:

$$\Lambda = \frac{L(m_i | H_0)}{\max_{p \in (0,1)} L(m_i | H_1)} \quad (8)$$

where $L(m_i|H_0)$ denotes the likelihood of observing $m_i$ under the null hypothesis that the match frequency and background frequency are equal (i.e. $p_i=q_i$) for a birth location i and $\max_{p \in (0,1)} L(m_i|H_1)$ denotes the likelihood of observing $m_i$ under the alternative hypothesis when varying p between 0 and 1. Thus, the test statistic is a ratio between a first likelihood of observing the match frequency and background frequency under the null hypothesis and a second likelihood of observing the match frequency and background frequency under the alternative hypothesis.

A summary statistic, $S_i$, is determined using $\Lambda$ according to:

$$S_i = -\log(\Lambda) = m_i \log \frac{p_i}{q_i} + (|M_u| - m_i) \log \frac{1-p_i}{1-q_i}, \quad (9)$$

The statistical analysis module 320 calculates a summary statistic for each birth location i. Note that if the match frequency, $p_i$, and background frequency, $q_i$, for a birth location received from the location frequency calculator 310 are equal, then the value of the summary statistic is zero. Additionally, the summary statistic $S_i$ increases in magnitude as the difference between the match frequency, $p_i$, and background frequency, $q_i$, increases in magnitude.

According to Wilks' theorem, as the sample size increases, twice the summary statistic $2S_i$ will follow a first order chi-squared distribution. Therefore, the statistical analysis model 320 may calculate the p-value for rejecting the null hypothesis $H_0$ based on the first order chi-squared distribution of the summary statistic, $S_i$.

For example at a significance level of 0.995 (p-value=$5 \times 10^{-3}$), the null hypothesis is rejected if $S_i > 4$ (or $2S_i > 8$) based on the first order chi-squared distribution. In other words, if the match frequency is sufficiently larger than the background frequency for a particular birthplace or surname such that the summary statistic $S_i > 4$, then the alternative hypothesis (i.e. where the match frequency does not equal the background frequency) is accepted. This indicates that the particular birthplace or surname is sufficiently notable to be associated with the ancestors of the individual 101.

The exact value of the significance level may vary by implementation, or according to more specific factors. Also, although the above embodiment describes the significance level as being a p-value, in practice it may be any threshold which determines whether or not a particular birth location i or surname j is sufficiently statistically significant to merit consideration for providing to the individuals.

For birth locations specifically, the statistical analysis module 320 may adjust the significance level (e.g., p-value) for a birth location i, based on the country of origin of the birth location. In various embodiments, the birth location i from a particular country of origin is determined based on the latitude and longitudinal coordinates associated with the birth location. More specifically, the particular significance level for a country of origin is chosen based on the number of users in the database associated with those countries in their respective pedigrees and the number of matches that a given individual has in the database that are annotated with a pedigree attached to them. For example, a birth location that derives from a country having a large number of users associated with that country (e.g., United States or Nordic countries) may utilize a relatively high significance level (e.g., 0.995), whereas a birth location that derives from a country having relatively few users associated with that country (e.g., Mexico, Russia, Eastern Europe) may utilize a relatively lower significance level (e.g., 0.9). Thus, depending upon the country, the threshold needed to determine whether the difference between the birth location match frequency versus the corresponding background frequency is statistically significant may vary. This allows the module 300 to better take into account the relative availability of data regarding a particular country in determining whether or not particular birth locations are statistically significant.

III.e Calculating the Enrichment Score

The statistical analysis module 320 determines which birth locations and surnames are statistically significant given the information known about them from the underlying pedigree data from users genetically matched to an individual 101. The enrichment score module 325 uses this binary determination of statistical significance to determine an enrichment score representing a strength of association between the birth location or surname and the ancestors of the individual 101.

To do this, the enrichment score module 325 determines an enrichment score, $x_i$, for each birth location, i, or enrichment score, $x_j$, for each surname, j. The enrichment score module 325 receives the summary statistic, $S_i$, for each birth location or the summary statistic, $S_j$, for each surname. Additionally, the enrichment score module 325 receives the match frequency, $p_i$ or $p_j$, and the background frequency, $q_i$ and $q_j$, for birth locations and surnames.

To calculate an enrichment score of a birth location, i, at the previously selected significance level of 0.995, the enrichment score module 325 calculates the enrichment score to be:

$$x_i = \begin{cases} p_i * \log\frac{p_i}{q_i} & \text{if } S_i > 4 \\ 0 & \text{otherwise} \end{cases} \quad (10)$$

The exact form of the calculation may vary in practice, particularly the significance level may vary by country as described above. Note that if the match frequency, $p_i$, and the background frequency, $q_i$, are not significantly different, then the enrichment score is close to zero, indicating that the particular birth location may not be very relevant to ancestors of the individual 101. Scaling the match frequency by a factor of log $$\frac{p}{q}$$

eliminates biases towards highly popular birth locations and surnames because they are likely to have a high background frequency (high q) as well, thereby reducing the enrichment score.

In one embodiments, the enrichment score module 325 calculates the enrichment score for a surname, j, in the same manner according to equation 10. In another embodiment, the enrichment score module 325 calculates the enrichment score for a surname, j, as $$x_j = p_j * \log\frac{p_j}{q_j} \quad (10)$$

for all summary statistic values.

The respective enrichment scores for a birth location and surname are stored in the location score store 380 and surname score store 390, respectively.

III.f Generating a List of Identified Birth Locations or Surnames

The enrichment score module 325 provides the enrichment score associated with each birth location or surname to the list generation module 330. The list generation module 330 may rank and/or provide one or more birth locations or surnames to the individual through client device 160 based on their associated enrichment scores. Exactly how the list generation module 330 provides birth locations and surnames, how many, and in what form (e.g., lists, etc.) may vary by implementation. In one embodiment, the list generation module 330 may set a minimum threshold in order for a particular birth location or surname to be recommended. For example, a birth location or surname may have to meet a certain minimum threshold enrichment score, and/or must appear in at least some number of pedigrees (e.g., $m_i \geq 3$) for it to be recommended.

In one embodiment, the list generation module 330 generates a list 370 including only the top N birth locations or surnames by enrichment score. The list 370 is sent through the network 120 to the client device 160 for consumption by the individual 101.

Identifying a Birth Location or Surname

Figure 4:
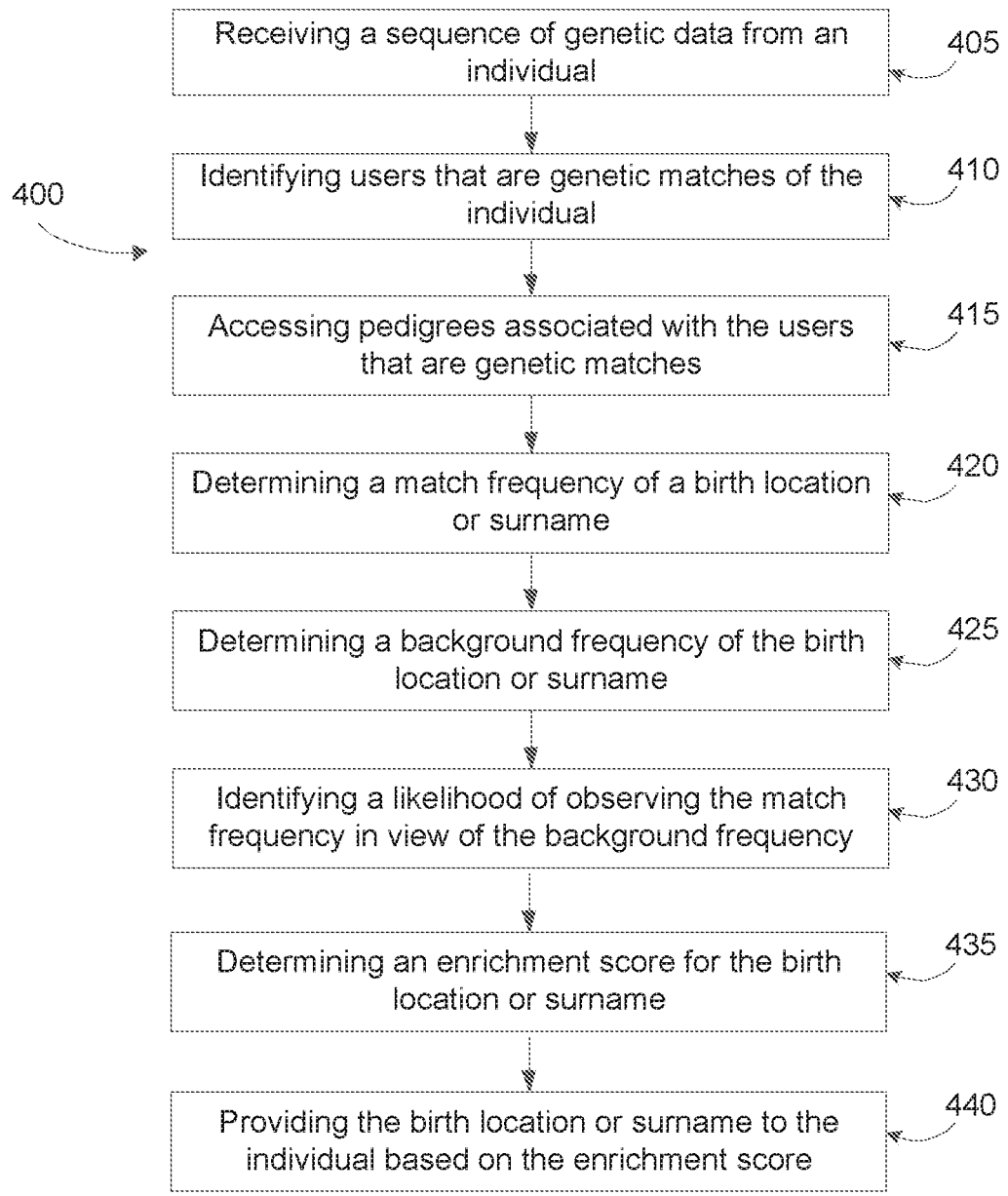
FIG. 4 is a flow diagram for identifying ancestral birthplace or surname identifications for an individual, in accordance with an embodiment.

FIG. 4 illustrates a process of providing an identified birth location or surname to an individual, according to one embodiment. The birth location and surname identification system 100 receives 405 a sequence of genetic data from an individual 101. The system 100 identifies users in the system 100 that are genetic matches with the individual 101. This may be accomplished by identifying DNA segment matches on the pair of haplotypes for the individual and the pair of haplotypes for users retrieved from the user data store 145.

Each user in the system 100 has a corresponding pedigree stored in the user data store 145. From the set of all pedigrees in the user data store 145, a subset of matching pedigrees is identified. Each pedigree in the subset of matching pedigrees is associated with a user that is a genetic match of the individual 101. The system 100 determines 420 a match frequency, p, of the birth location or surname amongst the subset of matching pedigrees. Additionally, the system 100 determines 425 a background frequency, q, of the birth location or surname amongst the set of all pedigrees.

The system 100 identifies 430 the likelihood of observing the match frequency and background frequency for a birth location or surname under the assumed scenario that the match frequency and background frequency are equal. The statistical analysis module 320 of the system 100 conducts a statistical test and determines 435 an enrichment score for each birth location or surname. Based on the statistical test and the enrichment score, the system may provide 440 the birth location or surname to the individual 101.

Additional Considerations

The birth location and surname identification system 100 is implemented using one or more computers having one or more processors executing application code to perform the steps described herein, and data may be stored on any conventional non-transitory storage medium and, where appropriate, include a conventional database server implementation. For purposes of clarity and because they are well known to those of skill in the art, various components of a computer system, for example, processors, memory, input devices, network devices and the like are not shown in FIG. 1. In some embodiments, a distributed computing architecture is used to implement the described features.

In addition to the embodiments specifically described above, those of skill in the art will appreciate that the invention may additionally be practiced in other embodiments. Within this written description, the particular naming of the components, capitalization of terms, the attributes, data structures, or any other programming or structural aspect is not mandatory or significant unless otherwise noted, and the mechanisms that implement the described invention or its features may have different names, formats, or protocols. Further, the system may be implemented via a combination of hardware and software, as described, or entirely in hardware elements. Also, the particular division of functionality between the various system components described here is not mandatory; functions performed by a single module or system component may instead be performed by multiple components, and functions performed by multiple components may instead be performed by a single component. Likewise, the order in which method steps are performed is not mandatory unless otherwise noted or logically required. It should be noted that the process steps and instructions of the present invention could be embodied in software, firmware or hardware, and when embodied in software, could be downloaded to reside on and be operated from different platforms used by real time network operating systems.

Algorithmic descriptions and representations included in this description are understood to be implemented by computer programs. Furthermore, it has also proven convenient at times, to refer to these arrangements of operations as modules or code devices, without loss of generality.

Unless otherwise indicated, discussions utilizing terms such as "selecting" or "determining" or "estimating" or the like refer to the action and processes of a computer system, or similar electronic computing device, that manipulates and transforms data represented as physical (electronic) quantities within the computer system memories or registers or other such information storage, transmission or display devices.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

The invention claimed is:

1. A method comprising:
   receiving, from an individual, at least one sequence of genetic data;
   accessing pedigrees of a set of users, each pedigree comprising a genealogical graph of relatives for one of the users;
   identifying a subset from the set of users, the subset having matching users, each matching user being a genetic match for the individual based on the at least one sequence of genetic data;
   determining a match frequency for a target birth location amongst the subset of matching users, determining the match frequency comprising:
     examining the pedigrees of the matching users in the subset;
     examining, for each matching user, birth locations of relatives in the pedigree of the matching user to determine whether there is at least one of the relatives whose birth location matches the target birth location;
     incrementing, for each matching user who has at least one of the relatives whose birth location matches the target birth location, a count of matching users; and
     determining the match frequency as a ratio of the count of the matching users over a total number of the matching users in the subset;
   determining a background frequency for the target birth location amongst the set of users determining the background frequency comprising:
     examining the pedigrees of the users in the set;
     examining, for each user, birth locations of relatives in the pedigree of the user to determine whether there is at least one of the relatives whose birth location matches the target birth location;
     incrementing, for each user who has at least one of the relatives whose birth location matches the target birth location, a count of users; and
     determining the background frequency as a ratio of the count of the users over a total number of the users in the set;
   calculating a summary statistic based on the match frequency and the background frequency, the summary statistics increases in magnitude as the difference between the match frequency and the background frequency increases in magnitude;
   determining an enrichment score for the birth location based on the summary statistic, the enrichment score representing a significance of the birth location to ancestors of the individual; and
   providing the birth location to a computing device based on the determined enrichment score for the birth location.

2. The method of claim 1 wherein the at least one sequence of genetic data comprises a pair of haplotypes for the individual.

3. The method of claim 2 wherein the subset of the set of users are Identity-By-Descent matches based on the pair of haplotypes for the individual and haplotypes of the set of users.

4. The method of claim 1 wherein calculating the summary statistic comprises:
   performing a maximum likelihood ratio test under the null hypothesis that the match frequency is equal to the background frequency.

5. The method of claim 1 wherein calculating the summary statistic comprises:
   determining a first likelihood of observing the match frequency and the background frequency for the birth location in view of a null hypothesis;
   determining a second likelihood of observing the match frequency and the background frequency for the birth location in view of an alternative hypothesis; and
   calculating a test statistic based on a ratio between the first likelihood and the second likelihood.

6. The method of claim 1 wherein determining the enrichment score for the birth location based on the summary statistic further comprises:
   determining whether the summary statistic is statistically significant relative to a statistical significance level; and
   calculating the enrichment score based on the determination.

7. The method of claim 6 wherein the significance level varies based on a country of origin of the birth location.

8. The method of claim 6 wherein the calculated enrichment score is based on the match frequency and the background frequency.

9. A method comprising:
   receiving, from an individual, at least one sequence of genetic data;
   accessing pedigrees of a set of users, each pedigree comprising a genealogical graph of relatives for one of the users;
   identifying a subset from the set of users, the subset having matching users, each matching user being a genetic match for the individual based on the at least one sequence of genetic data;
   determining a match frequency for a target surname amongst the subset of matching users, determining the match frequency comprising:
     examining the pedigrees of the matching users in the subset;
     examining, for each matching user, surnames of relatives in the pedigree of the matching user to determine whether there is at least one of the relatives whose surname matches the target surname;

incrementing, for each matching user who has at least one of the relatives whose surname matches the target surname, a count of matching users; and determining the match frequency as a ratio of the count of the matching users over a total number of the matching users in the subset;

determining a background frequency for the target surname amongst the set of users, determining the background frequency comprising:

examining the pedigrees of the users in the set;

examining, for each user, surnames of relatives in the pedigree of the user to determine whether there is at least one of the relatives whose surnames matches the target surname;

incrementing, for each user who has at least one of the relatives whose surname matches the target surname, a count of users; and determining the background frequency as a ratio of the count of the users over a total number of the users in the set;

determining an enrichment score for the surname based on a ratio of the match frequency to the background frequency, the enrichment score representing a significance of the surname to ancestors of the individual wherein the enrichment score increases in magnitude as the difference between the match frequency and the background frequency increases in magnitude; and providing the surname to a computing device based on the determined enrichment score for the surname.

10. The method of claim 9 wherein the at least one sequence of genetic data comprises a pair of haplotypes for the individual.

11. The method of claim 10 wherein the subset of the set of users are Identity-By-Descent matches based on the pair of haplotypes for the individual and haplotypes of the set of users.

12. The method of claim 9 further comprising:

determining a likelihood of observing the match frequency and the background frequency for the surname in view of a null hypothesis; and calculating a summary statistic based on the determined likelihood.

13. The method of claim 12 wherein calculating the summary statistic comprises:

performing a maximum likelihood ratio test under the null hypothesis that the match frequency is equal to the background frequency.

14. The method of claim 12 wherein calculating the summary statistic comprises:

determining a first likelihood of observing the match frequency and the background frequency for the surname in view of a null hypothesis;

determining a second likelihood of observing the match frequency and the background frequency for the surname in view of an alternative hypothesis; and calculating a test statistic based on a ratio between the first likelihood and the second likelihood.

15. The method of claim 14 wherein determining an enrichment score for the surname based on a ratio of the match frequency to the background frequency further comprises:

multiplying the match frequency by a logarithmic ratio between the match frequency and the background frequency.

16. The method of claim 9 wherein determining an enrichment score for the surname based on a ratio of the match frequency to the background frequency further comprises:

determining whether the summary statistic is statistically significant relative to a statistical significance level; and calculating the enrichment score based on the determination.

17. A non-transitory computer-readable medium comprising computer program code, the computer program code when executed by a processor causing the processor to perform steps comprising:

receiving, from an individual, at least one sequence of genetic data;

accessing pedigrees of a set of users, each pedigree comprising a genealogical graph of relatives for one of the users;

identifying a subset from the set of users, the subset having matching users, each matching user being a genetic match for the individual based on the at least one sequence of genetic data;

determining a match frequency for a target birth location amongst the subset of matching users, determining the match frequency comprising:

examining the pedigrees of the matching users in the subset;

examining, for each matching user, birth locations of relatives in the pedigree of the matching user to determine whether there is at least one of the relatives whose birth location matches the target birth location;

incrementing, for each matching user who has at least one of the relatives whose birth location matches the target birth location, a count of matching users; and determining the match frequency as a ratio of the count of the matching users over a total number of the matching users in the subset;

determining a background frequency for the target birth location amongst the set of users determining the background frequency comprising:

examining the pedigrees of the users in the set;

examining, for each user, birth locations of relatives in the pedigree of the user to determine whether there is at least one of the relatives whose birth location matches the target birth location;

incrementing, for each user who has at least one of the relatives whose birth location matches the target birth location, a count of users; and determining the background frequency as a ratio of the count of the users over a total number of the users in the set;

calculating a summary statistic based on the match frequency and the background frequency, the summary statistics increases in magnitude as the difference between the match frequency and the background frequency increases in magnitude;

determining an enrichment score for the birth location based on the summary statistic, the enrichment score representing a significance of the birth location to ancestors of the individual; and providing the birth location to a computing device based on the determined enrichment score for the birth location.

18. A non-transitory computer-readable medium comprising computer program code, the computer program code when executed by a processor causing the processor to perform steps comprising:

receiving, from an individual, at least one sequence of genetic data;

accessing pedigrees of a set of users, each pedigree comprising a genealogical graph of relatives for one of the users;

identifying a subset from the set of users, the subset having matching users, each matching user being a genetic match for the individual based on the at least one sequence of genetic data;

determining a match frequency for a target surname amongst the subset of matching users, determining the match frequency comprising:
  examining the pedigrees of the matching users in the subset;
  examining, for each matching user, surnames of relatives in the pedigree of the matching user to determine whether there is at least one of the relatives whose surname matches the target surname;
  incrementing, for each matching user who has at least one of the relatives whose surname matches the target surname, a count of matching users; and
  determining the match frequency as a ratio of the count of the matching users over a total number of the matching users in the subset;

determining a background frequency for the target surname amongst the set of users, determining the background frequency comprising:
  examining the pedigrees of the users in the set;
  examining, for each user, surnames of relatives in the pedigree of the user to determine whether there is at least one of the relatives whose surnames matches the target surname;
  incrementing, for each user who has at least one of the relatives whose surname matches the target surname, a count of users; and
  determining the background frequency as a ratio of the count of the users over a total number of the users in the set;

determining an enrichment score for the surname based on a ratio of the match frequency to the background frequency, the enrichment score representing a significance of the surname to ancestors of the individual wherein the enrichment score increases in magnitude as the difference between the match frequency and the background frequency increases in magnitude; and providing the surname to a computing device based on the determined enrichment score for the surname.

* * * * *